United States Patent
Pang et al.

(10) Patent No.: US 11,219,583 B2
(45) Date of Patent: Jan. 11, 2022

(54) COMPOSITIONS COMPRISING ALCOHOL-RICH MIXTURES OF ALCOHOL AND PROPYLENE GLYCOL METHYL ETHERS

(71) Applicant: L'OREAL, Paris (FR)

(72) Inventors: Christopher Pang, New York, NY (US); Tsang-Min Huang, Scotch Plains, NJ (US); I-Fan Hsieh, Scotch Plains, NJ (US)

(73) Assignee: L'OREAL, Paris (FR)

( * ) Notice: Subject to any disclaimer, the term of this patent is extended or adjusted under 35 U.S.C. 154(b) by 92 days.

(21) Appl. No.: 16/426,105

(22) Filed: May 30, 2019

(65) Prior Publication Data

US 2020/0375858 A1    Dec. 3, 2020

(51) Int. Cl.
*C11D 3/14* (2006.01)
*A61K 8/34* (2006.01)
*A61K 8/39* (2006.01)
*A61K 8/49* (2006.01)
*A61Q 3/04* (2006.01)

(52) U.S. Cl.
CPC ............... *A61K 8/34* (2013.01); *A61K 8/39* (2013.01); *A61K 8/4973* (2013.01); *A61Q 3/04* (2013.01)

(58) Field of Classification Search
CPC ....... C11D 3/201; C11D 3/2068; C11D 7/263; C11D 7/5077; C11D 7/5086
See application file for complete search history.

(56) References Cited

U.S. PATENT DOCUMENTS

| | | | |
|---|---|---|---|
| 5,486,305 A | 1/1996 | Faryniarz et al. | |
| 5,772,988 A * | 6/1998 | Pagano | A61K 8/8152 424/61 |
| 5,866,104 A | 2/1999 | Cataneo et al. | |
| 6,156,711 A | 12/2000 | Perlman | |
| 6,379,356 B1 | 4/2002 | Jackson | |
| 6,689,727 B1 * | 2/2004 | Olsson | A61K 8/0208 510/118 |
| 6,841,523 B1 | 1/2005 | Holtz | |
| 7,074,746 B2 | 7/2006 | Fujii | |
| 2001/0003735 A1 * | 6/2001 | Perlman | A61K 8/737 510/118 |
| 2005/0202982 A1 * | 9/2005 | Perlman | A61K 8/4973 510/118 |
| 2010/0204076 A1 * | 8/2010 | Cheng | A61K 8/39 510/118 |
| 2011/0056517 A1 * | 3/2011 | Motsenbocker | C11D 3/43 134/6 |
| 2012/0196788 A1 * | 8/2012 | Motsenbocker | C11D 7/5027 510/473 |
| 2013/0053298 A1 * | 2/2013 | Holzhauer | C11D 3/386 510/505 |
| 2014/0309153 A1 * | 10/2014 | Valkonen | C11D 3/201 510/118 |
| 2014/0328612 A1 * | 11/2014 | Knoeller | A45D 34/042 401/269 |
| 2015/0015951 A1 * | 1/2015 | Takebe | G02B 5/305 359/489.07 |
| 2015/0053888 A1 * | 2/2015 | Taguchi | C09K 13/06 252/79.4 |
| 2017/0007516 A1 * | 1/2017 | Mercado | A61K 8/345 |
| 2018/0207309 A1 * | 7/2018 | Salowitz | A61L 9/01 |
| 2018/0250925 A1 * | 9/2018 | Merka | C25D 11/12 |
| 2020/0002645 A1 * | 1/2020 | Hunt, Jr. | C11D 7/266 |
| 2020/0147254 A1 * | 5/2020 | Lombard | A61L 9/14 |
| 2020/0324527 A1 * | 10/2020 | Klun | B32B 3/266 |

FOREIGN PATENT DOCUMENTS

| | | | |
|---|---|---|---|
| CN | 104263554 | * | 1/2015 |
| CN | 104263554 A | | 1/2015 |
| EP | 1591101 | * | 2/2005 |
| EP | 1591101 A1 | | 11/2005 |
| JP | 2018083818 A | | 5/2018 |
| WO | 0012052 A1 | | 3/2000 |
| WO | 2015135021 | * | 9/2015 |
| WO | 2015135021 A1 | | 9/2015 |

OTHER PUBLICATIONS

Nail Polish Fast Remover, Mintel GNPD, Record ID 5748165, p. 1-4 Published on Jun. 13, 2018.
International Search report and Written Opinion dated Jul. 16, 2020 in corresponding PCT application No. PCT/US2020/034042.

* cited by examiner

*Primary Examiner* — Charles I Boyer
(74) *Attorney, Agent, or Firm* — Meagher Emanuel Laks Goldberg & Liao, LLP.

(57) ABSTRACT

A composition for removing nail polish includes a propylene glycol methyl ether; and a C2-C3 monoalcohol. The C2-C3 monoalcohol and the propylene glycol methyl ether are present in a C2-C3 monoalcohol to propylene glycol methyl ether ratio by weight from about 1:1 to about 20:1. Methods for removing nail polish are also provided.

13 Claims, No Drawings

COMPOSITIONS COMPRISING ALCOHOL-RICH MIXTURES OF ALCOHOL AND PROPYLENE GLYCOL METHYL ETHERS

FIELD OF THE INVENTION

The present invention relates to compositions and methods for removing nail polish.

DISCUSSION OF THE BACKGROUND

Nail polish compositions are typically designed to provide long-lasting color to nails. Because of the materials used in nail polish compositions to obtain the desired properties, it has proven difficult to remove such nail polish compositions from nails without adversely affecting the nails.

In particular, the inventors have recognized the need to provide efficacious nail polish removal.

SUMMARY OF THE INVENTION

The present invention relates to compositions for removing nail polish that include a propylene glycol methyl ether and a C2-C3 monoalcohol. The C2-C3 monoalcohol and the propylene glycol methyl ether are present in a C2-C3 monoalcohol to propylene glycol methyl ether ratio by weight from about 1:1 to about 20:1.

The present invention also relates to methods for removing nail polish from nails of a human subject. The method includes applying a composition to the nails of a subject onto which the nail polish had been previously applied and removing the nail polish from the nails. The compositions for removing nail polish include a propylene glycol methyl ether; and a C2-C3 monoalcohol. The C2-C3 monoalcohol and the propylene glycol methyl ether are present in a C2-C3 monoalcohol to propylene glycol methyl ether ratio by weight from about 1:1 to about 20:1.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations. All percentages listed are by weight unless otherwise noted.

Numerical ranges are inclusive of endpoints and meant to include all combinations and sub-combinations. For example, from about 5%, 10% or 15% to about 20%, 50% or 60% means about 5% to about 20%, about 5% to about 50%, about 5% to about 60%, about 10% to about 20%, about 10% to about 50%, about 10% to about 60%, about 15% to about 20%, about 15% to about 50%, or about 15% to about 60%.

Other than in the operating examples, or where otherwise indicated, all numbers expressing quantities of ingredients and/or reaction conditions are to be understood as being modified in all instances by the term "about," meaning within 10% of the indicated number, such as within about 5%, such as within 1% or 2% of the indicated number.

"Essentially free" means that the composition includes less than about 3% of the identified ingredient. "Substantially free" means that the composition contains less than about 2% of the identified ingredient. "Free" means that the composition contains less than 1% of the identified ingredient.

"Nail" as used herein includes fingernails as well as toenails.

The compositions, coats and methods of the present invention can comprise, consist of, or consist essentially of the essential elements and limitations of the invention described herein, as well as any additional or optional ingredients, components, or limitations described herein or otherwise useful. In certain embodiments, compositions of the invention consist of or consist essentially of a propylene glycol methyl ether and a C2-C3 monoalcohol, wherein the C2-C3 monoalcohol and the propylene glycol methyl ether are present in a C2-C3 monoalcohol to propylene glycol methyl ether ratio by weight from about 1:1 to about 20:1, such as from about 1:1 to about 9:1.

For purposes of the compositions and methods of the present invention where the invention "of" the identified ingredients and/or process steps, the "basic and novel properties" of such compositions and/or methods is removing nail polish from nails.

Compositions for Removing Nail Polish

The inventors have found that in general neither C2-C3 monoalcohols nor propylene glycol methyl ethers alone remove nail polish well. However, surprisingly certain mixtures of these two ingredients work very well at removing nail polish.

C2-C3 monoalcohol

In accordance with the present invention, compositions for removing nail polish comprising a C2-C3 monoalcohol are provided.

"C2-C3 monoalcohol" means an alcohol having 2 or 3 carbon atoms such as ethanol, propanol, and isopropanol. In certain embodiments the C2-C3 monoalcohol is ethanol.

The C2-C3 monoalcohol is present in the compositions of the present invention in an amount of from about 5%, 10%, 15%, 25%, or 50% by weight to about 50%, 70% or 95% by weight. In certain notable embodiments, the C2-C3 monoalcohol is present in a concentration of at least about 50%, such as from about from about 50% to about 90%

Propylene Glycol Methyl Ether

In accordance with the present invention, compositions for removing nail polish comprise a propylene glycol methyl ether. Propylene glycol methyl ethers are a particular class of glycol ethers that are generally made by reacting propylene oxide with methanol. Examples of propylene glycol methyl ethers include propylene glycol methyl ether ($C_4H_{10}O_2$; e.g., DOWANOL PM), dipropylene glycol methyl ether ($C_7H_{16}O_3$; e.g., DOWANOL DPM), and tripropylene glycol methyl ether ($C_{10}H_{22}O_4$; e.g., DOWANOL TPM). DOWANOL products are commercially available from Dow Chemical of Midland, Mich.

According to certain embodiments, the propylene glycol methyl ether is selected from dipropylene glycol methyl ether, tripropylene glycol methyl ether, and combinations thereof. According to certain other embodiments, the propylene glycol methyl ether is tripropylene glycol methyl ether.

The propylene glycol methyl ether may be present in the composition in an amount from about 0.5%, 1%, 2%, 3%, 5% or 10% to about 10%, 20%, 30%, 40% or 50% by weight. In certain notable embodiments, the nail polish-removing solvent is present in a concentration from about 3% to about 20%, such as about 3% to about 10%.

C2-C3 monoalcohol to Propylene Glycol Methyl Ether Weight Ratio

The inventors have found that highly efficacious nail polish removal may be performed using alcohol-rich mixtures of alcohol and propylene glycol methyl ether. By "alcohol-rich mixtures of alcohol and propylene glycol methyl ether" it is meant that the C2-C3 monoalcohol and the propylene glycol methyl ether are present in a C2-C3 monoalcohol to propylene glycol methyl ether ratio by weight from that is from about 1:1 to about 20:1. This means that the concentrations by weight of the C2-C3 monoalcohol and the propylene glycol methyl ether are at one extreme about equal to each other. At the other extreme the concentration by weight of the C2-C3 monoalcohol is about twenty times more than the concentration by weight of the propylene glycol methyl ether. In certain other embodiments, the C2-C3 monoalcohol to propylene glycol methyl ether ratio by weight from that is from about 1:1 to about 9:1, such as from about 2:1 to about 9:1. In certain other embodiments, the C2-C3 monoalcohol to propylene glycol methyl ether ratio by weight is as described in this paragraph and the concentration of C2-C3 monoalcohol is at least about 50% by weight.

Thickening Agent

In accordance with the present invention, compositions for removing nail polish comprising at least one thickening agent are provided. Non-limiting examples of thickening agents that may be used according to various embodiments of the present invention include those conventionally used in cosmetics, such as polymers of natural origin and synthetic polymers. For example, nonionic, anionic, cationic, amphiphilic, and amphoteric polymers, and other known rheology modifiers, such as cellulose-based thickeners, may be used.

According to certain embodiments, the thickening agent is a cellulose-based thickener. Suitable cellulose-based compounds include, but are not limited to, cellulose polymers, such as, for example, hydroxyethylcellulose, hydroxypropylcellulose, methylcellulose, and ethylhydroxyethylcellulose. Certain notable cellulose derivatives include hydroxyl-modified cellulose polymers such as Hydroxyethylcellulose, e.g., those having a molecular weight over 500,000 daltons such as NATROSOL 250 HHR and Hydroxypropyl cellulose, e.g.,KLUCEL MF—both available from Ashland of Covington, Ky.

According to other embodiments, the thickening agent is a polysaccharide.

In general, polysaccharides may be divided into several categories. Polysaccharides that are suitable for use in the invention may be homopolysaccharides such as fructans, glucans, galactans and mannans or heteropolysaccharides such as hemicellulose.

Suitable polysaccharides may be linear polysaccharides such as pullulan or branched polysaccharides such as gum arabic and amylopectin, or mixed polysaccharides such as starch. Suitable polysaccharides may be starchy polysaccharides. Starchy polysaccharides include, but are not limited to, native starches, modified starches and particulate starches.

According to other embodiments, the thickening agent is an acrylic thickening agent (acrylic thickener) or an acrylamide thickening agent (acrylamide thickener).

"Acrylic thickening agent" or "acrylic thickener" as used herein refers to polymers based upon one or more (meth) acrylic acid (and corresponding (meth)acrylate) monomers or similar monomers.

"Acrylamide thickening agent" or "acrylamide thickener" as used herein refers to polymers based upon one or more acrylamide monomers or similar monomers.

According to other embodiments, the thickening agent comprises at least one monomer performing a weak acid function such as, for example, acrylic acid, methacrylic acid, itaconic acid, crotonic acid, maleic acid and/or fumaric acid.

According to other embodiments, the thickening agent comprises at least one monomer performing a strong acid function such as, for example, monomers having a function of the sulfonic acid type or phosphonic acid type, such as 2-acrylamido-2-methylpropane sulfonic acid (AMPS).

According to other embodiments, the thickening agent may be crosslinked (or branched). Suitable examples of acceptable crosslinking agents include, but are not limited to, methylene bisacrylamide (MBA), ethylene glycol diacrylate, polyethylene glycol dimethacrylate, diacrylamide, cyanomethacrylate, vinyloxyethacrylate or methacrylate, formaldehyde, glyoxal, and compositions of the glycidylether type such as ethyleneglycol diglycidylether, or epoxides.

Suitable acrylic thickeners are disclosed in U.S. patent application publication nos. 2004/0028637 and 2008/0196174, the entire contents of both of which are incorporated herein by reference.

Specific non-limiting examples of suitable thickening agents include homopolymers or copolymers of acrylic or methacrylic acids or the salts thereof and the esters thereof, such as the products sold under the names VERSICOL F® or VERSICOL K® by Allied Colloid, ULTRAHOLD 8® by Ciba-Geigy, polyacrylates and polymethacrylates such as the products sold under the names LUBRAJEL and NORGEL by Guardian, or under the name HISPAJEL by Hispano Chimica, polyacrylic acids of SYNTHALEN K type, polyacrylamides, copolymers of acrylic acid and of acrylamide sold in the form of the sodium salt thereof, such as under the names RETEN® by Hercules, the sodium polymethacrylate such as sold under the name DARVAN 7® by Vanderbilt, and the sodium salts of polyhydroxycarboxylic acids such as sold under the name HYDAGEN F® by Henkel, optionally crosslinked and/or neutralized 2-acrylamido-2-methylpropanesulphonic acid polymers and copolymers, for instance poly(2-acrylamido-2-methylpropanesulphonic acid) such as sold by Clariant under the name HOSTACERIN AMPS (INCI name: ammonium polyacryldimethyltauramide), crosslinked anionic copolymers of acrylamide and of AMPS, e.g. in the form of a water-in-oil emulsion, such as those sold under the name SEPIGEL® 305 (CTFA name: Polyacrylamide/C13-14 lsoparaffin/Laureth-7) and under the name SIMULGEL® 600 (INCI name: Acrylamide/Sodium acryloyldimethyltaurate copolymer/Isohexa-decane/Polysorbate 80) by SEPPIC, polyacrylic acid/alkyl acrylate copolymers of PEMULEN type, sodium acrylate/sodium acryloyldimethyl taurate such as that sold under the INCI name Sodium Acrylate/Sodium Acryloyldimethyl Taurate Copolymer & Hydrogenated Polydecene & Sorbitan Laurate & Trideceth-6 which is marketed by Lonza, Allendale, N.J., USA under the tradename ViscUp®EZ. Certain especially notable acrylic thickeners are selected from the group of: Acrylamide/Sodium Acryloyldimethyl Taurate Copolymer such as those provided in Isohexadecane & Polysorbate 80 as SIMULGEL 600 and SIMULGEL 800; Polyacrylamide provided with C13-14 isoparaffin and laureth-7 available as SEPIGEL 305; and Polyacrylate Crosspolymer-6 available as SEPIMAX ZEN. SIMULGEL, SEPIGEL, and SEPIMAX products are available from Seppic Inc. of Paris, France. In certain embodiments, the thickening agent is selected from polyacrylamides and water soluble cellulose polymers (such as hydroxypropylmethylcellulose, ethylcellulose, and/or hydroxypropylcellulose), and combinations thereof.

According to other embodiments, the thickening agent is an organoclay (hydrophobically treated clay) or a hydrophilic clay. The term "hydrophilic clay" means a clay that is capable of swelling in water; this clay is activated in water and forms after hydration a colloidal dispersion. These clays are products that are already well known per se, which are described, for example, in the book "Mineralogie des argiles", S. Caillere, S. Henin, M. Rautureau, $2^{nd}$ edition 1982, Masson, the teaching of which is included herein by way of reference. Clays are silicates containing a cation that may be chosen from calcium, magnesium, aluminium, sodium, potassium and lithium cations, and mixtures thereof. Examples of such products that may be mentioned include clays of the smectite family such as montmorillonites, hectorites, bentonites, beidellites and saponites, and also of the family of vermiculites, stevensite and chlorites. These clays may be of natural or synthetic origin. Hydrophilic clays that may be mentioned include smectite products such as saponites, hectorites, montmorillonites, bentonites and beidellite.

The term "lipophilic clay" (or hydrophobically treated clay) means a clay that is capable of swelling in a lipophilic medium; this clay swells or becomes "activated" in a hydrophobic solvent and thus forms a colloidal dispersion. Examples of lipophilic clays that may be mentioned include modified clays such as modified hectorite, such as those modified with a $C_{10}$ to C22 fatty-acid ammonium chloride. Examples include hectorite modified with distearyldimethylammonium chloride (INCI name: disteardimonium hectorite).

In particular, among the thickening agents that may be used, mention may be made of silica particles. Suitable silicas include, but are not limited to, hydrophobic synthetic amorphous silicas, pyrogenic or fumed silica optionally with hydrophobic surface treatment with particle size less than 10 microns, such as less than 500 nm, such as less than 100 nm, such as from 5 nm to 30 nm, including all ranges and subranges therebetween.

The at least one thickening agent may be present in the compositions of the present invention in an amount greater than 0.05% by weight, such as greater than 0.1% by weight, such as greater than 0.5% by weight, such as greater than 1% by weight and such as less than 15% by weight, including all ranges and subranges therebetween such as, for example, from 0.1% to 15%, such as from 0.1% to 10%, such as from 0.5% to 10%, such as from 0.75% to 7.5%, such as from 1% to 5%, etc., with all weights being based on the weight of the composition.

While in certain notable embodiments, the composition is a single phase, in certain other embodiments, the composition may comprise multiple phases.

According to certain other embodiments, the composition may include a single multicomponent (solution) phase including the C2-C3 monoalcohol and the propylene glycol methyl ether, and further include a suspended solid phase that is suspended in the multicomponent solution phase. The suspended solid phase may include any of various ingredients that do not dissolve in the multicomponent solution phase and are capable of being suspended therein. According to certain notable embodiments, the suspended solid phase includes one or more abrasive compounds.

Abrasive Compound

In accordance with the present invention, compositions for removing nail polish comprising at least one abrasive compound (abrasive system) are provided. A "abrasive compound" is a compound capable of providing abrasion or mechanical exfoliation and in accordance with the present invention has one or more of the following characteristics:

(1) Surface roughness: particles with irregular edges provide for abrasion; (2) shape: the particles of the abrasive compound may have a non-angular shape such as a disc, oval or sphere; (3) average particle size: in the context of abrasive compounds from mineral origins, shells, seeds micronized fruit kernel powders, and the like. The particles of the abrasive may have a particle size of 1000 microns (µm) or less, such as 500 µm or less, such as 300 µm or less, such as 150 µm or less, such as 75 µm or less, such as, 50 µm or less such as 30 µm or less; and (4) hardness: the abrasive particles may be soft so as to provide for mild abrasion. According to certain embodiments, the abrasive of the present invention has at least two of the above-mentioned properties, such as at least three of the above-mentioned properties, such as all four of the above-mentioned properties. For example—the abrasive compound may be a large spherical material and not hard; or very small, hard, and having an irregular shape. The hardness may be between (inclusive of endpoints) 3-8 (Mohs hardness); or between 40-60 (Shore D hardness) if the compound is a wax or polymer.

The abrasive of the present invention may have at least two of the above-mentioned properties, such as at least three of the above-mentioned properties, and such as all four of the above-mentioned properties.

Suitable non-limiting examples of abrasive compounds include, but are not limited to, water-soluble abrasives such as sugars; and/or water-insoluble abrasives such as ground fruit kernel or shell powders, materials such as perlite, pumice or apricot kernel, coconut scrubs, zeolites, hydrated silica, calcium carbonate, dicalcium phosphate dihydrate, calcium pyrophosphate, alumina, sodium bicarbonate, polylactic acid, spherical waxes (for example, jojoba scrubeads), as well as synthetic polymeric materials such as polyethylene, polypropylene, polyethylene terephthalate, polymethyl methacrylate or nylon.

The at least one abrasive compound may be present in the compositions of the present invention in an amount greater than 0.5% by weight, such as greater than 1% by weight, such as greater than 2.5% by weight, such as greater than 5% by weight such as less than 40% by weight, including all ranges and subranges therebetween such as, for example, from 0.5% to 40%, such as from 1% to 30%, such as from 2.5% to 25%, such as from 5% to 20%, etc., with all weights being based on the weight of the composition. However, it is to be understood that these weight amounts in this paragraph refer to the total amount of abrasive compound present, including those particles which particles of the abrasive compound used in accordance with the present invention which do not have the smoothness, shape, size and/or surface roughness characteristics discussed above.

The suspended solid phase may include other particulate material such as pigments, optical modifiers, tactile modifiers, and the like.

According to certain embodiments, the compositions may comprise another solvent useful for removing nail polish such as a high boiling point ester compound. By "high boiling point ester compound" means an ester compound having a boiling point greater than 90° C. The high boiling point ester compound may have a boiling point greater than 125° C., such as greater than 175° C., and such as greater than 200° C.

Suitable high boiling point ester compounds include, but are not limited to, esters of C4-C22 dicarboxylic or tricarboxylic acids and of C1-C22 alcohols, such as C1-C8 alcohols, and such as C1-C3 alcohols. Notable high boiling point ester compounds include carbonate esters, adipates, sebacates and succinates. Specific examples of high boiling point ester compounds include, but are not limited to, alkylene carbonates such as propylene carbonate, dimethyl succinate, diethyl succinate, dimethyl glutarate, diethyl glutarate, dimethyl sebacate, diethyl sebacate, diisopropyl sebacate, bis(2-ethylhexyl) sebacate, dimethyl adipate, diisopropyl adipate, di-n-propyl adipate, dioctyl adipate, bis(2-ethylhexyl) adipate, diisostearyl adipate, ethyl maleate, bis (2-ethylhexyl) maleate, triisopropyl citrate, triisocetyl citrate, triisostearyl citrate, trioctyldodecyl citrate and trioleyl citrate.

According to certain embodiments, compositions of the present invention may be essentially free, substantially free, or free of certain ingredients. One such ingredient is gamma-butyrolactone. Another such ingredient is acetone. Yet another of such ingredients is glycerin. Yet another of such ingredients are alkylene carbonates.

While in certain embodiments, the compositions may include oils, in certain embodiments of the invention are essentially free, substantially free, or free of oils. As used herein, by "oils," it is meant compounds having a melting point of less than about 30° C. and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the oil does not include hydroxyl moieties.

Suitable examples of compounds of oils include vegetable oils (glyceryl esters of fatty acids, monoglycerides, diglycerides, triglycerides) and fatty esters. Specific non-limiting examples include, without limitation, esters such as isopropyl palmitate, isopropyl myristate, isononyl isonanoate $C_{12}$-$C_{15}$ alkyl benzoates, caprylic/capric triglycerides, ethylhexyl hydroxystearate, silicone oils (such as dimethicone and cyclopentasiloxane), pentaerythritol tetraoctanoate and mineral oil. Other examples of oils include liquid organic ultraviolet filter commonly used for example as UV-absorbing sunscreens such as octocrylene, octyl salicylate, octyl methoxyxcinnamate, among others.

Auxiliaries/Additives

The compositions discussed above may additionally comprise an additive or auxiliary commonly used in cosmetic compositions and known to a person skilled in the art as being capable of being incorporated into a nail polish remover composition. Such additives or auxiliaries may be chosen from solvents, preservatives, fragrances, waxes, surfactants, antioxidants, agents for combating free radicals, wetting agents, dispersing agents, antifoaming agents, neutralizing agents, stabilizing agents, active principles chosen from moisturizing agents, vitamins, proteins, ceramides, plant extracts, fibers, and the like, and their mixtures.

A person skilled in the art will take care to select the optional additional additives and/or the amount thereof such that the advantageous properties of the compositions according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 40% (such as from 0.01% to 15%) relative to the total weight of the composition.

Needless to say, the compositions of the invention should be cosmetically or dermatologically acceptable, i.e., they should contain a non-toxic physiologically acceptable. The compositions may be in any galenic form normally employed in the cosmetic and dermatological fields which is suitable for topical administration onto nails.

The compositions according to the invention can be manufactured by known processes used generally in the cosmetics or dermatological field.

According to certain embodiments, methods of removing nail polish from nails comprising applying a composition for removing nail polish described above to nails onto which nail polish has been previously applied and removing the nail polish from the nails are provided.

According to certain other embodiments, methods of removing nail polish from nails (and optionally moisturizing hands) include the steps of applying a composition for removing nail polish described above to the hands as well as to the nails onto which nail polish has been previously applied (i.e., onto coatings formed on human nails); and removing the nail polish from the nails. According to certain other embodiments, the compositions are applied not only to nails to remove nail polish but also to the hands to moisturize them. The composition may also be rinsed from the hands and nails such as with water. In certain embodiments, compositions of the present invention may be advantageously used without an absorbent pad (otherwise commonly used to remove nail polish from the nails).

The nail polish to be removed according to the methods described herein may be solvent based nail polish having nitrocellulose film-former. Alternatively, the nail polish to be removed may be a water-based nail polish that includes water dispersible polymers such as acrylic lattices and the like.

According to yet other embodiments, compositions of the present invention are used to remove other forms of makeup such as mascara, foundation, or pigmented compositions that had previously been applied to the hair Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Examples

Example I(a)

Removability

An experiment was conducted to assess removability of nail polish using nineteen compositions that included various combinations of ingredients. These ingredients included one or more of ethanol, propylene glycol methyl ether(s), glycerin, and propylene carbonate. The compositions were prepared by combining the ingredients in the relative concentrations by weight listed below and mixing to homogeneity. Nail polish (ESSIE Russian Roulette nail lacquer available from L'Oreal SA of Paris, France) films were prepared using a 6 mil bird bar to drawdown the film over a Leneta Opacity Card substrate. The cards were allowed to dry for 24 hours. Then a drop (0.01 gram) of each remover solution was placed on the surface of the nail polish film. After each time point, the remover was wiped off using Kimberly Clark napkins. The removal efficacy was assessed at the three different time points 30 s/60 s/150 s. The observation was recorded in Table 1, below where L=little to no removal, M=medium removal, H=high (best) removal.

TABLE 1

Nail Polish Removability

| Ref. | Ethanol Conc. | Dipropylene glycol methyl ether Conc. | Tripropylene glycol methyl ether Conc. | Propylene carbonate Conc. | Glycerin Conc | Removal Performance (30 s/60 s/150 s) |
|---|---|---|---|---|---|---|
| A |  |  | 100 |  |  | L/L/M |
| B |  |  | 75 | 25 |  | L/L/H |
| C |  |  | 50 | 50 |  | L/M/H |
| D |  |  | 25 | 75 |  | L/H/H |
| E |  |  |  | 100 |  | M/H/H |
| F | 0 | 100 |  |  |  | L/M/M |
| G | 50 | 50 |  |  |  | H/H/H |
| H | 100 | 0 |  |  |  | L/L/L |
| I | 33 |  |  | 33 | 33 | L/L/H |
| J | 33 |  | 33 | 33 |  | M/H/H |
| K | 25 |  | 25 | 25 | 25 | L/L/H |
| L |  |  | 100 |  |  | L/L/M |
| M | 50 |  | 50 |  |  | H/H/H |
| N | 100 |  |  |  |  | L/L/L |
| O | 50 |  |  | 50 |  | M/H/H |
| P | 10 |  | 90 |  |  | M/M/H |
| Q | 25 |  | 75 |  |  | M/M/H |
| R | 75 |  | 25 |  |  | H/H/H |
| S | 90 |  | 10 |  |  | H/H/H |

The results indicate surprisingly good nail polish removal for compositions with alcohol-rich mixtures of alcohol and propylene glycol methyl ethers having a C2-C3 monoalcohol to propylene glycol methyl ether ratio by weight from about 1:1 to about 20:1.

What is claimed is:

1. A composition for removing nail polish, consisting essentially of:
   a propylene glycol methyl ether;
   a C2-C3 monoalcohol;
   a thickening agent;
   an optional abrasive compound; and
   an optional alkylene carbonate;
   wherein the C2-C3 monoalcohol and the propylene glycol methyl ether are present in a C2-C3 monoalcohol to propylene glycol methyl ether ratio by weight from about 1:1 to about 20:1,
   wherein the propylene glycol methyl ether comprises dipropylene glycol methyl ether, tripropylene glycol methyl ether, or a combination thereof,
   wherein the thickener is a cellulose-based thickener, a polysaccharide, an acrylic thickener, an organoclay, a hydrophilic clay, silica, or a combination thereof.

2. The composition according to claim 1, wherein the composition includes the optional abrasive compound, wherein the abrasive is a sugar, a ground fruit kernel or shell powder, perlite, pumice, a coconut-based abrasive, a zeolite, hydrated silica, calcium carbonate, dicalcium phosphate dihydrate, calcium pyrophosphate, alumina, sodium bicarbonate, polylactic acid, a spherical wax, polyethylene, polypropylene, polyethylene terephthalate, polymethlyl methacrylate, nylon, or a combination thereof.

3. The composition according to claim 2, wherein the composition is free of oils.

4. The composition according to claim 2, wherein the composition includes the optional alkyl carbonate.

5. The composition according to claim 4, wherein the thickener is a polysaccharide, an organoclay, a hydrophilic clay, silica, or a combination thereof.

6. The composition according to claim 5, wherein the propylene glycol methyl ether is tripropylene glycol methyl ether and the C2-C3 monoalcohol is ethanol.

7. The composition according to claim 1, wherein the composition comprises at least about 50% by weight of the C2-C3 monoalcohol.

8. The composition according to claim 7, wherein the composition comprises between about 3% to about 10% by weight of the propylene glycol methyl ether.

9. A method of removing nail polish comprising applying to a nail polish coating formed on a human nail a composition consisting of:
   a propylene glycol methyl ether;
   a C2-C3 monoalcohol;
   a thickening agent;
   an optional abrasive compound; and
   an optional alkylene carbonate;
   wherein the C2-C3 monoalcohol and the propylene glycol methyl ether are present in a C2-C3 monoalcohol to propylene glycol methyl ether ratio by weight from about 1:1 to about 20:1, wherein the propylene glycol methyl ether comprises dipropylene glycol methyl ether, tripropylene glycol methyl ether, or a combination thereof, wherein the thickener is a cellulose-based thickener, a polysaccharide, an acrylic thickener, an organoclay, a hydrophilic clay, silica, or a combination thereof.

10. The method according to claim 9, wherein the composition includes the optional abrasive compound, wherein the abrasive is a sugar, a ground fruit kernel or shell powder, perlite, pumice, a coconut-based abrasive, a zeolite, hydrated silica, calcium carbonate, dicalcium phosphate dihydrate, calcium pyrophosphate, alumina, sodium bicarbonate, polylactic acid, a spherical wax, polyethylene, polypropylene, polyethylene terephthalate, polymethlyl methacrylate, nylon, or a combination thereof.

11. The method according to claim 10, wherein the thickener is a polysaccharide, an organoclay, a hydrophilic clay, silica, or a combination thereof.

12. The method according to claim 11, wherein the propylene glycol methyl ether is tripropylene glycol methyl ether and the C2-C3 monoalcohol is ethanol.

13. The method according to claim 12, wherein the composition comprises at least about 50% by weight of the C2-C3 monoalcohol.

* * * * *